United States Patent [19]
Rice et al.

[11] Patent Number: 6,046,228
[45] Date of Patent: Apr. 4, 2000

[54] ANTI-VIRAL PHARMACEUTICAL COMPOSITIONS CONTAINING SATURATED 1,2-DITHIAHETEROCYCLIC COMPOUNDS AND USES THEREOF

[75] Inventors: William G. Rice, Frederick; Robert R. Schultz, Gaithersburg, both of Md.; David C. Baker, Knoxville, Tenn.; Louis E. Henderson, New Market, Md.

[73] Assignee: The United States of America as represented by the Department of Health and Human Services, Washington, D.C.

[21] Appl. No.: 09/214,331

[22] PCT Filed: Jul. 3, 1997

[86] PCT No.: PCT/US97/10870

§ 371 Date: Jan. 4, 1999

§ 102(e) Date: Jan. 4, 1999

[87] PCT Pub. No.: WO98/01440

PCT Pub. Date: Jan. 15, 1998

Related U.S. Application Data

[60] Provisional application No. 60/021,665, Jul. 5, 1996.

[51] Int. Cl.[7] ............... A61K 31/385; C07D 339/02; C07D 409/00
[52] U.S. Cl. ............ 514/441; 514/442; 514/440; 514/436; 549/35; 549/36; 549/37; 549/38; 549/39; 549/21
[58] Field of Search ............... 549/35, 36, 37, 549/38, 39, 21, 20, 22; 514/440, 441, 442, 436

[56] References Cited

U.S. PATENT DOCUMENTS

| | | | |
|---|---|---|---|
| 3,158,621 | 11/1964 | Klingsberg et al. | 549/35 |
| 5,334,612 | 8/1994 | Kalden et al. | 514/440 |
| 5,470,871 | 11/1995 | Christen et al. | 514/441 |
| 5,693,460 | 12/1997 | Lok | 549/35 |
| 5,925,668 | 7/1999 | Biewenga et al. | 514/440 |

FOREIGN PATENT DOCUMENTS

| | | |
|---|---|---|
| 0318891 | 6/1989 | European Pat. Off. . |
| 0427246 | 5/1991 | European Pat. Off. . |
| 2148296 | 5/1985 | United Kingdom . |
| 9208717 | 5/1992 | WIPO . |
| 9609406 | 3/1996 | WIPO . |

*Primary Examiner*—Deborah C. Lambkin
*Attorney, Agent, or Firm*—Townsend and Townsend and Crew

[57] ABSTRACT

The present invention is directed to pharmaceutical compositions including a saturated 1,2-dithiaheterocyclic compound having antiviral activity. The present invention also provides a kit containing the pharmaceutical composition and methods of treating or preventing viral disease using the composition, as well as methods for inactivating retrovirus in a body fluid.

21 Claims, 5 Drawing Sheets

ANTI-VIRAL PHARMACEUTICAL COMPOSITIONS CONTAINING SATURATED 1,2-DITHIAHETEROCYCLIC COMPOUNDS AND USES THEREOF

This application is a 371 of PCT/US97/10870 Jul. 3, 1997 Provisional Application No. 60/021,665 Jul. 5, 1995.

GOVERNMENT SUPPORT

The work described in this application was supported in part by research contracts NO1-CM-17551 and NO1-CM-48038 from the National Cancer Institute. The United States Government may have certain rights in this invention.

BACKGROUND OF THE INVENTION

Numerous compounds are currently undergoing in vitro development and clinical evaluation as potential drugs for the treatment of human immunodeficiency virus type 1(HIV-1) infection and the associated acquired immunodeficiency syndrome (AIDS). Historically, compounds directed toward inhibition of virus attachment to target cells have failed clinically due to their toxicities at effective antiviral concentrations, poor absorption from the gut or lack of broad spectrum activities against clinical stains of HIV-1. Similarly, the approach to use synthetic nucleoside analogs, such as 3'-azido-3'-deoxythymidine (AZT), or the complex class of non-nucleoside compounds to target the HIV-1 reverse transcriptase (RT) enzyme has been plagued by the emergence of drug-resistant strains. HIV-1 protease has also become the focus of much attention as a potential antiviral target due to its critical role in the post-integration processing of viral precursor polypeptides to their mature products, a process required for maturation of virus particles into infectious virions. Unfortunately, the vast majority of designed inhibitors of protease are substrate-based peptide structures that typically demonstrate poor bioavailability, short serum half-lives and overt cytotoxicity at effective antiviral concentration.

In addition, most antiviral drugs used to control the spread of HIV-1 have also proven to become compromised under the selection pressure of the drug, as the virus soon mutates to a drug-resistant strain. This tendency to develop drug resistance is a survival strategy used by many classes of viruses and is particularly pronounced among the members of the retrovirus family. One way to defeat this survival strategy is to focus on drugs attacking specific elements of the virus that are intolerant to mutations. Such elements can be identified by searching the proteins present in all viruses within the virus class to identify common or highly conserved structures.

Retroviruses have a highly conserved structure in their nucleocapsid (NC) proteins. All NC proteins of the Oncoviridae and Lentiviridae subfamilies of Retroviridae contain sequences of 14 amino acids with 4 invariant residues, $Cys(X)_2Cys(X)_4His(X)_4Cys$, which chelate zinc through histidine imidazole and cysteine thiolates with a $K_d$ less than $10^{-13}$. These structures are referred to as retroviral CCHC zinc fingers, and are one of the most highly conserved features of retroviruses (Henderson, et al., *J. Biol. Chem.* 256:8400–8406 (1981)). Examples of retroviruses which possess at least one CCHC type zinc finger per nucleocapsid protein include, but are not limited to, HIV-1, HIV-2, SIV, BIV, EIAV, Visna, CaEV, HTLV-1, BLV, MPMV, MMTV, RSV, MuLV, FeLV, BaEV, and SSV. Due to their highly conserved nature, it is thought that CCHC zinc fingers perform an essential function in viral infectivity. In fact, it has been disclosed that mutations of the chelating residues (CCHC) in the zinc fingers yield a non-infectious virus (Gorelick, et al., *J. Virol.* 64:3207–3211 (1990)).

HIV-1 NC contains two zinc finger domains separated by only 7 amino acids. HIV-1 NC proteins are synthesized as part of the $Pr55^{gag}$ and $Pr160^{gag-pol}$ precursor polyproteins, and the fingers within these precursor molecules are required for packaging of viral genomic RNA and to form the core structure of the immature virion. Subsequent proteolytic processing of these precursors yields the mature p7NC protein, and the fingers of the NC protein are required for the virus to fully execute reverse transcription in the next target cell. Hence, treating of HIV-1 infected individuals with antiviral compounds that target the mutationally intolerant retroviral zinc finger may provide for multiple inhibitory effects on the viral replication cycle while attenuating the emergence of drug-resistant HIV-1 strains.

Widespread acceptance of the CCHC zinc finger as an antiviral target has not been forthcoming due to a lack of identification of compounds that selectively target that structure. Recently, however, it has been demonstrated that the two CCHC zinc fingers of the HIV-1 p7NC protein are susceptible to electrophilic attack by certain electrophilic reagents (nitrosos, disulfides, disulfoxides, maleamides, peroxides, and others), resulting in covalent modification of the Cys sulfur atoms and functional inactivation of the fingers.

For example, it has been shown that the CCHC zinc fingers could be specifically attacked by the thiolate-reactive C-nitroso compounds, resulting in inactivation of HIV-1 and SIV infectivity (Rice et al., *Nature* 361:473–475 (1993)).

The action of the electrophilic C-nitroso compounds is through a chemical attack of the compound on the nucleophilic zinc-coordinating cysteine thiolates, with subsequent ejection of zinc from the structure; the action is not mediated by a chelation effect.

In addition to the C-nitroso compounds, a second class of compounds has been found which targets the zinc finger of retroviruses. This second class of compounds falls into the general class of disulfide benzamides (DIBAs) (Rice et al., *Science* 270: 1194–1197, (1995)). It has been shown that the DIBAs are capable of inhibiting retroviruses. The compounds do not affect virus binding to cells or the activities of purified HIV-1 reverse transcriptase or integrase, and protease inhibition does not correlate with antiviral activity in culture. The DIBAs directly inactivate HIV- 1 virions by entering the virions and cross-linking the p7NC proteins. In addition, DIBAs inhibit the production of infectious virus from previously infected cells by acting on the zinc fingers in the Gag precursor polyproteins. The compounds are also synergistic with other antiviral agents and drug-resistant mutants have not arisen. Moreover, the DIBA compounds do not affect the activity of proteins tested to date that contain the classical type CCCC or CCHH zinc finger motifs.

Despite the promising antiviral activity of the DIBA type compounds, there is the possibility that in vivo the sulfur atoms in these compounds could be reduced. The resultant two inactive monomers could disassociate resulting in a loss of antiviral activity.

SUMMARY OF THE INVENTION

The present invention is directed to pharmaceutical compositions that include a saturated 1,2-dithiaheterocyclic compound and/or a pharmaceutically acceptable salt thereof, together with a pharmaceutically acceptable carrier. Suitable saturated 1,2-dithiaheterocyclic compounds include 1,2-dithiane and 1,2 dithiolane compounds. The ring sulfur atoms of the 1,2-dithiaheterocyclic compounds can be in a number of different oxidation states, i.e., the ring sulfur atoms may be present in the —S—, —S(O)— or —SO$_2$- oxidation state. The 1,2-dithiaheterocyclic compounds may optionally be substituted on one or more of the ring carbon atoms with a variety of common substituents. Examples of suitable substituent groups which may be present on the 1,2-dithiaheterocyclic ring include hydroxy, hydroxyalkyl, alkyl, cycloaklyl, carboxyalkyl, acyl, acyloxyalkyl, —C(O)OH, —C(O)O—R$^5$ (where R$^5$ is an alkyl, cycloalkyl or aryl group), acyloxy, aryl, —OSO$_2$R$^6$ (where R$^6$ is an alkyl, cycloalkyl or aryl group), and —NR$^7$R$^8$ (where R$^7$ and R$^8$ are independently hydrogen, alkyl, cycloalkyl or aryl).

The present invention also provides a kit containing the pharmaceutical composition and methods of treating or preventing viral disease using the composition, as well as methods for inactivating retrovirus in a body fluid.

DETAILED DESCRIPTION OF THE INVENTION

Figure 1A:
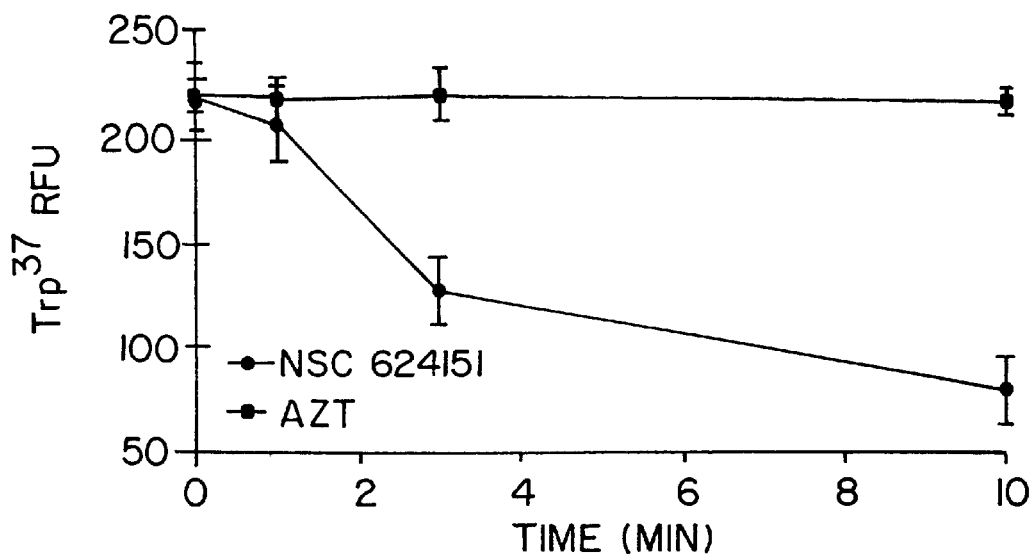
FIG. 1(A) is a graph which illustrates the time dependent loss of fluorescence caused by NSC 624151 but not by AZT control. NSC 624151 promotes zinc ejection, but DDC, UC38 and KNI-272 compounds do not.

The present invention is directed to pharmaceutical compositions including a saturated 1,2-dithiaheterocyclic compound or a pharmaceutically acceptable salt of such a compound. As used herein, a saturated 1,2-dithiaheterocyclic compound refers to a saturated, cyclic compound with a ring containing and two adjacent sulfurs. As used herein, saturated 2-dithiaheterocyclic compound refers to a substituted or unsubstituted saturated 1,2-dithiaheterocyclic compound. One or more carbon atoms of the ring system can be substituted with a variety of common substituents, such as hydroxy, hydroxyalkyl, alkyl, cycloalkyl, carboxyalkyl, acyl, acyloxyalkyl, —C(O)OH, —C(O)O—R$^5$ (where R$^5$ is an alkyl, cycloalkyl or aryl group), acyloxy, aryl, —OSO$_2$R$^6$ (where R$^6$ is an alkyl, cycloalkyl or aryl group), and —NR$^7$R$^8$ (where R$^7$ and R$^8$ are independently hydrogen, alkyl, cycloalkyl or aryl). In addition, the sulfur atoms of the ring can be present in several different oxidation states. Preferably one of the sulfur atoms is present in the —S(O)— or —SO$_2$— oxidation state. In one embodiment the saturated 1,2-dithiaheterocyclic compound can include a ring oxygen atom that is not adjacent to a ring sulfur atom.

The saturated 1,2-dithiaheterocyclic compound is typically a 1,2-dithiane or 1,2-dithiolane compound. As used herein, a 1,2-dithiane compound is a saturated, cyclic compound with a ring containing four carbons and two, adjacent sulfur atoms; and a 1,2-dithiolane compound is a saturated, cyclic compound with a ring containing three carbons and two, adjacent sulfur atoms. Thus, 1,2-dithiane and 1,2-dithiolane are homologous compounds, and corresponding substituted 1,2-dithianes and substituted 1,2-dithiolanes are homologous. As used herein, 1,2dithiane or 1,2dithiolane refers to a substituted or unsubstituted 1,2-dithiane or 1,2-dithiolane, respectively.

One or more of the ring carbon atoms can be substituted with a variety of common substituents. Suitable substituents include hydroxy, hydroxyalkyl, alkyl, cycloalkyl, alkoxy, cycloalkoxy, carboxyalkyl, acyl, —C(O)OH, —C(O)O—R$^5$ (where R$^5$ is an alkyl, cycloalkyl or aryl group), acyloxy, aryl, —OSO$_2$R$^6$ (where R$^6$ is an alkyl, cycloalkyl or aryl group), and —NR$^7$R$^8$. These substituents may themselves be substituted with functional groups such as a hydroxy group, a carboxy group, an acetoxy group, or a halogen. For example, one of the ring carbon atoms of the 1,2-dithiaheterocyclic compound may be substituted with a halogenated alkyl group (e.g., a trifluoromethyl group) or a hydroxyalkyl group (e.g., —CH$_2$OH). Two substituents on the same or adjacent ring carbons may be joined to form a cyclic ring, e.g. a spiro-hydantoin ring. Such cyclic ring substituents typically have from 3 to 7 atoms and preferably 5 or 6 atoms in the ring.

The individual substituents present on the 1,2-dithiaheterocyclic compound typically have no more than about 10 carbon atoms, and preferably no more than about 6 carbon atoms. Examples of particularly suitable substituents include hydroxy, C(1)–C(3)hydroxyalkyl, C(1)–C(3) acyloxy (e.g., acetoxy), and C(2)–C(4)acyloxyalkyl groups.

The 1,2-dithiolane and 1,2-dithiane compound can have one of the following general structures A and B, respectively:

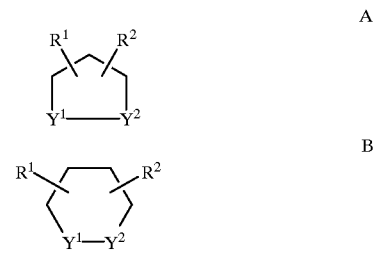

In structures A and B, R$^1$ and R$^2$ can individually be a variety of common substituents. Suitable R$^1$ and R$^2$ substituents include hydroxy, hydroxyalkyl, alkyl, cycloalkyl, alkoxy, cycloalkoxy, carboxyalkyl, acyl, acyloxyalkyl, —C(O)OH, —C(O)O—R$^5$ (where R$^5$ is an alkyl, cycloalkyl or aryl group), acyloxy, aryl, —OSO$_2$R$^6$ (where R$^6$ is an alkyl, cycloalkyl or aryl group), and —NR$^7$R$^8$. The R$^1$ and R$^2$ substituents may themselves be substituted with functional groups such as a hydroxy group or a halogen. For example, one of the ring carbon atoms of the 1,2-dithiaheterocyclic compound may be substituted with a halogenated alkyl group (e.g., a trifluoromethyl group) or a hydroxyalkyl group (e.g., —CH$_2$OH). The R$^1$ and R$^2$ substituents present on the 1,2-dithiaheterocyclic compound typically have no more than about 10 carbon atoms, and preferably no more than about 6 carbon atoms. Examples of particularly suitable $R^1$ and $R^2$ substituents include hydroxy, $C(1)$–$C(3)$hydroxyalkyl, $C(1)$–$C(3)$acyloxy (e.g., acetoxy), and $C(2)$–$C(4)$acyloxyalkyl groups.

In structures A and B, $Y^1$ and $y^2$ are sulfur. $Y^1$ and $Y^2$ can individually be in any of several oxidation states, such as —S—, —S(O)— or —SO$_2$—. Preferably one of $Y^1$ or $Y^2$ is —S(O)— or —SO$_2$—. More preferably one of $Y^1$ or $Y^2$ is —SO$_2$—.

Preferably, in structure A, $R^1$ and $R^2$ are independently hydrogen, hydroxy, $C(1)$–$C(3)$hydroxyalkyl, acetoxy, or $C(2)$–$C(4)$acyloxyalkyl. More preferably, in structure A, $R^1$ and $R^2$ are independently hydroxy, —CH$_2$OH, acetoxy, or —CH$_2$OAc. More preferably, in structure A, $R^1$ and $R^2$ are CH$_2$OH; $Y^1$ is —S—; and $Y^2$ is —SO$_2$—.

Preferably, in structure B, $R^1$ and $R^2$ are independently hydrogen, hydroxy, $C(1)$–$C(3)$hydroxyalkyl, acetoxy, or $C(2)$–$C(4)$acyloxyalkyl. More preferably, in structure B, $R^1$ and $R^2$ are independently hydroxy, —CH$_2$OH, acetoxy, or —CH$_2$OAc. More preferably, in structure B, $R^1$ and $R^2$ are independently hydroxy, —CH$_2$OH, acetoxy, or —CH$_2$OAc; and $Y^1$ is —S— and $Y^2$ is —S(O)— or —SO$_2$—. More preferably, in structure B, $R^1$ and $R^2$ are hydroxy; and $Y^1$ is —S— and $Y^2$ is —S(O)— or —SO$_2$—.

Preferably, the 1,2-dithiolane and 1,2-dithiane compound has one of the following general structures C and D, respectively:

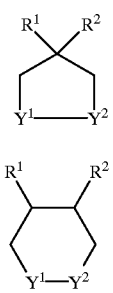

C

D

In structures C and D, $R^1$ and $R^2$ can individually be a variety of common substituents. Suitable $R^1$ and $R^2$ substituents include hydroxy, hydroxyalkyl, alkyl, cycloalkyl, alkoxy, cycloalkoxy, carboxyalkyl, acyl, —C(O)OH, —C(O)O—$R^5$ (where $R^5$ is an alkyl, cycloalkyl or aryl group), acyloxy, aryl, —OSO$_2$$R^6$ (where $R^6$ is an alkyl, cycloalkyl or aryl group), and —NR$^7$R$^8$. The $R^1$ and $R^2$ substituents may themselves be substituted with functional groups such as a hydroxy group or a halogen. For example, one of the ring carbon atoms of the 1,2-dithiaheterocyclic compound may be substituted with a halogenated alkyl group (e.g., a trifluoromethyl group) or a hydroxyalkyl group (e.g., —CH$_2$ OH). The $R^1$ and $R^2$ substituents present on the 1,2-dithiaheterocyclic compound typically have no more than about 10 carbon atoms, and preferably no more than about 6 carbon atoms. Examples of particularly suitable $R^1$ and $R^2$ substituents include hydroxy, $C(1)$–$C(3)$ hydroxyalkyl, $C(1)$–$C(3)$acyloxy (e.g., acetoxy), and $C(2)$ –$C(4)$acyloxyalkyl groups.

In structures C and D, $Y^1$ and $Y^2$ are sulfur. $Y^1$ and $Y^2$ can individually be in any of several oxidation states, such as —S—, —S(O)— or —SO$_2$—. Preferably one of $Y^1$ or $Y^2$ is —S(O)— or —SO$_2$—. More preferably one of $Y^1$ or $Y^2$ is —SO$_2$—.

Preferably, in structure C, $R^1$ and $R^2$ are independently hydrogen, hydroxy, $C(1)$–$C(3)$hydroxyalkyl, acetoxy, or $C(2)$–$C(4)$acyloxyalkyl. More preferably, in structure C, $R^1$ and $R^2$ are independently hydroxy, —CH$_2$OH, acetoxy, or —CH$_2$OAc. More preferably, in structure C, $R^1$ and $R^2$ are CH$_2$OH; $Y^1$ is —S—; and $Y^2$ is —SO$_2$—.

Preferably, in structure D, $R^1$ and $R^2$ are independently hydrogen, hydroxy, $C(1)$–$C(3)$hydroxyalkyl, acetoxy, or $C(2)$–$C(4)$acyloxyalkyl. More preferably, in structure D, $R^1$ and $R^2$ are independently hydroxy, —CH$_2$OH, acetoxy, or —CH$_2$OAc. More preferably, in structure D, $R^1$ and $R^2$ are independently hydroxy, —CH$_2$OH, acetoxy, or —CH$_2$OAc; $Y^1$ is —S—; and $Y^2$ is —SO$_2$—. More preferably, in structure D, $R^1$ and $R^2$ are hydroxy; $Y^1$ is —S—; and $Y^2$ is —SO$_2$—.

More preferably, the 1,2-dithiolane and 1,2-dithiane compound has one of the following general structures E and F, respectively:

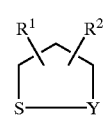

E

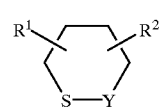

F

In structure E and F, $R^1$ and $R^2$ are independently hydrogen, hydroxy, $C(1)$–$C(3)$hydroxyalkyl, acetoxy, or $C(2)$–$C(4)$ acyloxyalkyl; and Y is —S—, —S(O)— or —SO$_2$—.

More preferably, the 1,2-dithiolane and 1,2-dithiane compound has one of the following general structures G and H, respectively:

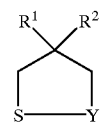

G

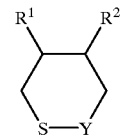

H

In structures G and H, $R^1$ and $R^2$ are independently hydroxy, —CH$_2$OH, acetoxy, or —CH$_2$OAc; and Y is —S(O)— or —SO$_2$—. Preferably, in structure G, $R^1$ and $R^2$ are CH$_2$OH; and Y is —SO$_2$—. Preferably in structure H, $R^1$ and $R^2$ are hydroxy; and Y is —SO$_2$—.

Compounds with the 4 position of the dithiolane ring is substituted with both amino and carboxy groups, or protected forms thereof, are particularly suitable for use in the present invention. Examples of such dithiolanes include compounds having NSC numbers 208750 and 212561 (see Table 1) and analogs where the dithiolane ring includes —SO— or —SO$_2$—. Similarly dithianes having either the 4 or 5 position substituted with both amino and carboxy groups, or protected forms thereof, are particularly suitable for use in the present invention.

The 1,2-dithiane or 1,2-dithiolane compounds include compounds of the following general formulas (I) or (II)

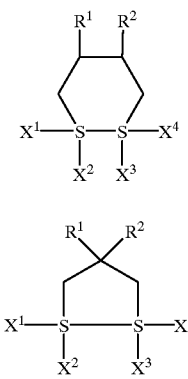

wherein $R^1$ and $R^2$ are each selected independently of each other and are typically selected from the group consisting of hydrogen, $CH_2OH$, a unsubstituted or substituted cyclic group of 4–7 carbons wherein the substituent on said cyclic group is a lower alkyl of 1–4 carbons and $OR^3$, wherein $R^3$ is selected from the group consisting of a hydrogen atom, a lower alkyl group containing 1–4 carbons and $SO_2R^4$ wherein $R^4$ is selected from the group consisting of a hydrogen atom, a lower alkyl of 1–4 carbons and a unsubstituted or substituted cyclic group of 4–7 atoms wherein the substituent of said cyclic group is a lower alkyl of 1–4 carbons. $X^1$–$X^4$ are either an oxygen atom or are not present, e.g., —$S(X^1)(X^2)$— is either —S—, —S(O)— or —$SO_2$—. Preferably both $X^1$–$X^2$ is oxygen and the $X^3$ and $X^4$ are not present.

When $R^1$, $R^2$ and $R^4$ are cyclic groups of 4–7 carbons, such groups can be saturated or unsaturated groups as well as aromatic groups, including cyclopentyl, phenyl and cyclohexyl. When $R^1$, $R^2$ and $R^4$ are saturated cyclic groups, the ring can include an oxygen atom.

Preferably, the present 1,2-dithiaheterocyclic compound includes at least one ring carbon atom having a hydroxy-functional substituent. The 1,2-dithiaheterocyclic compound may include two hydroxy-functional substituents on the same ring carbon atom and/or may have hydroxy-functional substituents on two or more ring carbon atoms. As used herein, the term "hydroxy-functional substituent" includes any substituent bearing a hydroxy group. Examples of suitable hydroxy-functional substituents include hydroxy, hydroxy-substituted alkyl groups, hydroxy-substituted cycloalkyl groups. Other suitable hydroxy-functional substituents include hydroxyacetyloxy; —C(O)O—$R^5$, where $R^5$ is alkyl, cycloalkyl, hydroxyalkyl, or hydroxycycloalkyl; —$OSO_2R^6$, where $R^6$ is alkyl, cycloalkyl, hydroxyalkyl, or hydroxycycloalkyl; and —$NR^7R^8$ groups, where at least one of $R^7$ and $R^8$ is alkyl, cycloalkyl, hydroxyalkyl, or hydroxycycloalkyl.

1,2-Dithiolane and 1,2-dithiane compounds having two hydroxy-functional substituents are particularly suitable 1,2-dithiaheterocyclic compounds for use in the present invention. If the 1,2-dithiaheterocyclic compound is a 1,2-dithiolane compound, the ring carbon atom at the 4-position preferably bears two hydroxy-functional substituents. More preferably, the 4-position of the 1,2-dithiolane compound is substituted with two —$CH_2OH$ substituents. If the 1,2-dithiaheterocyclic compound is a 1,2-dithiane compound, the ring carbon atoms at the 4- and 5-positions preferably each bear a single hydroxy-functional substituent. More preferably, the 1,2-dithiane compound is substituted at each of the 4- and 5-positions with a single hydroxy group. One example of such a compound which is particularly effective in the present invention is the (−)-enantiomer of cis-1,1-dioxo[1,2]dithiane-4,5-diol.

Another group of preferable substituents are those substituents bearing a functional group capable of being converted into a hydroxy-functional group. Examples of such groups include sulfonate ("—$OSO_2R^6$"), acyloxy groups (which are capable of being hydrolyzed to generate a hydroxy group), and acyloxyalkyl groups (which are capable of being hydrolyzed to generate a hydroxy group).

The pharmaceutical compositions of the present invention are useful as antiviral agents and are particularly effective at inhibiting the replication of retroviruses and for treating retroviral pathologies. The saturated 1,2-dithiaheterocyclic compounds of the pharmaceutical compositions of the present invention target the zinc finger of the nucleocapsid protein and can react with the nucleophilic sulfur atoms of the zinc fingers through the electrophilic sulfur groups of the compounds.

The present compounds and corresponding pharmaceutical compositions have an advantageous property over the previously known bis-type DIBA compounds because of the tethering of the sulfur groups. Because of the tethering of the sulfur groups, the present saturated 1,2-dithiaheterocyclic compounds, if reduced in vivo, will not dissociate forming two inactive monomers.

It has been determined, however, that simply tethering a compound containing a sulfur group into a cyclic compound does not result in an active antiviral compound. In addition to the presence of the sulfur groups, it has been further determined that the antiviral activity of the present compounds is enhanced by the oxidation of at least one of the sulfur moieties.

Thus, the saturated 1,2-dithiaheterocyclic compounds of the present invention can inhibit viral growth through the inactivation of the zinc finger due to the sulfur and monoxide or dioxide moieties (e.g. —S—, —SO— or —$SO_2$—). In addition, the present compounds have the advantage over compounds of the prior art in that they will not dissociate in vivo into two inactive monomers.

The present saturated 1,2-dithiaheterocyclic compounds can be used in pharmaceutical compositions for treatment of viral pathologies. It is anticipated that the pharmaceutical compositions of the present invention can be used to treat any viral disease which is caused by a retrovirus, as the zinc finger targeted by the present compositions are conservatively found with retroviruses. Retroviruses which can be treated by the present compositions include, but are not limited to HIV-1, HIV-2, SIV, BIV, EIAV, Visna, CaEV, HTLV-1, BLV, MPMV, MMTV, RSV, MuLV, FeLV, BaEV, and SSV. Preferably, the compositions of the invention are useful for treatment of HIV.

The pharmaceutical compositions of the present invention include a saturated 1,2-dithiaheterocyclic compound in effective unit dosage form and a pharmaceutically acceptable carrier. As used herein, the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, which are preferably non-toxic, and can be solid, liquid, or gaseous materials, which are otherwise inert and medically acceptable and are compatible with the active ingredients.

Water, saline, aqueous dextrose, and glycols are preferred liquid carriers, particularly (when isotonic) for injectable solutions. The carrier can be selected from various oils, including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical expedients, such as sterilization, and can contain conventional pharmaceutical additives, such as preservatives, stabilizing agents, wetting, or emulsifying agents, salts for adjusting osmotic pressure, buffers, and the like. Suitable pharmaceutical carriers and their formulations are described in Martin, "Remington's Pharmaceutical Sciences," 15th Ed.; Mack Publishing Co., Easton (1975); see, e.g., pp. 1405–1412 and pp. 1461–1487. Such compositions will, in general, contain an effective amount of the active compound together with a suitable amount of carrier so as to prepare the proper dosage form for proper administration to the host.

The pharmaceutical compositions can contain other active ingredients such as antimicrobial agents, other antiviral agents, and other agents such as preservatives. Additional antiviral agents which can be included in the pharmaceutical compositions of the present invention include, but are not limited to, nucleoside analog reverse transcriptase inhibitors such as AZT, ddC, 3TC and acyclovir; non-nucleoside reverse transcriptase inhibitors such as nevirapine, TIBO, BHAP, etc.; surface-active agents which prevent the virus from binding to the cells, including Farmatalia distamycin derivatives, dextran sulfate, ISIS 5320 and resobene; Costatolide, and protease inhibitors such as KNI-272.

These pharmaceutical compositions can be administered parenterally, including by injection; orally; used as a suppository or pessary; applied topically as an ointment, cream, aerosol, powder; or given as eye or nose drops, etc., depending on whether the preparation is used to treat internal or external viral infections.

The compositions can contain 0.1% –99% of the active material. For topical administration, for example, the composition will generally contain from 0.01% to 20%, and more preferably 0.5% to 5% of the active material.

The present invention is also drawn to methods of treating viral diseases using the present pharmaceutical compositions. Typically, the compositions will be administered to a patient (human or other animal, including mammals such as, but not limited to, cats, horses and cattle and avian species) in need thereof, in an effective amount to inhibit the viral replication. The present compositions can be given either orally, intravenously, intramuscularly or topically.

For oral administration, fine powders or granules can contain diluting, dispersing and/or surface active agents, and can be presented in a draught, in water or in a syrup; in capsules or sacnets in the dry state or in a non-aqueous solution or suspension, wherein suspending agents can be included; in tablets or enteric coated pills, wherein binders and lubricants can be included; or in a suspension in water or a syrup. Where desirable or necessary, flavoring, preserving, suspending, thickening, or emulsifying agents can be included. Tablets and granules are preferred, and these can be coated.

For buccal administration, the compositions can take the form of tablets or lozenges formulated in a conventional manner.

For parenteral administration or for administration as drops, as for eye infections, the compounds can be presented in aqueous solution in a concentration of from about 0.1 to 10%, more preferably 0.5 to 2.0%, most preferably 1.2% w/v. The solution can contain antioxidants, buffers, etc.

The compositions according to the invention can also be formulated for injection and can be presented in unit dose form in ampoules or in multi-dose containers with an added preservative. The compositions can take such forms as suspensions, solutions, or emulsions in oily or aqueous vehicles, and can contain formulatory agents such as suspending, stabilizing, and/or dispersing agents. Alternatively, the active ingredient can be in powder form for constitution with a suitable vehicle, e.g., sterile, pyrogen-free buffer saline, before use. The present compositions can also be in the form of encapsulated liposomes.

Alternatively, for infections of the eye or other external tissues, e.g., mouth and skin, the compositions are preferably applied to the infected part of the body of the patient as a topical ointment or cream. The compounds can be presented in an ointment, for instance with a water-soluble ointment base, or in a cream, for instance with an oil in water cream base, in a concentration of from about 0.1 to 10%, preferably 0.5 to 2.0%, most preferably 1.2% w/v. For topical administration, the daily dosage as employed for adult human treatment will range from 0.1 mg to 1000 mg, preferably 0.5 mg to 10 mg. However, it will be appreciated that extensive skin infections can require the use of higher doses.

The compositions can also be applied into body orifices such as the nose, oral cavity and ears in the form of a spray or drops. For example, the compositions can be applied into body orifices such as the rectum and vagina in the form of a suppository or cream.

For systemic administration, the daily dosage as employed for adult human treatment will range from 5 mg to 5000 mg of active ingredient, preferably 50 mg to 2000 mg, which can be administered in 1 to 5 daily doses, for example, depending on the route of administration and the condition of the patient. When the compositions include dosage units, each unit will preferably contain 2 mg to 2000 mg of active ingredient, for example 50 mg to 500 mg. For serious infections, the compound can be administered by intravenous infusion using, for example, 0.01 to 10 mg/kg/hr of the active ingredient.

The present invention further encompasses a method of treating blood supplies, body fluid samples or other material which can potentially be contaminated with a virus. For example, a composition of the present invention can be included in a tube or other sample device used for obtaining a fluid sample from a patient, human or other animal, which is potentially infected with a retrovirus. The presence of the composition in the sample device will inactivate the virus when the sample is obtained, thus reducing the risk to the sample handler. The composition of the present invention can be supplied from a manufacturer in pre-packaged sample devices or, alternatively, the compositions can be added to the sample devices by the end user in an appropriate amount to inactivate the virus.

The present invention is further drawn to pharmaceutical compositions and methods of using thereof for the prevention of the transmission of viral infection. It is, thus, anticipated that the present pharmaceutical compositions can be used as a prophylaxis against virus infection. As such, the present compositions can be in the form of an emulsion ointment or cream, and can be applied intravaginally or topically. The compositions of the present invention can be further combined with additional antiviral, spermicidal, bacteriacidal and/or lubricating agents.

The present invention also encompasses a kit including the present pharmaceutical compositions and to be used with the methods of the present invention. The kit can contain a vial which contains a saturated 1,2-dithiaheterocyclic compound of the present invention and suitable carriers, either dried or liquid form. The kit further includes instructions in the form of a label on the vial and/or in the form of an insert included in a box in which the vial is packaged, for the use and administration of the compounds. The instructions can also be printed on the box in which the vial is packaged. The instructions contain information such as sufficient dosage and administration information so as to allow a worker in the field to administer the drug. It is anticipated that a worker in the field encompasses any doctor, nurse, or technician who might administer the drug.

The present invention may be better understood with reference to the following examples. These examples are intended to be representative of specific embodiments of the invention, and are not intended as limiting the scope of the invention.

EXAMPLES

I. Virus Replication Inhibition Assays.

Initial anti-HIV screening was performed with CEM-SS cells and HIV-1$_{RF}$ using the XTT cytoprotection assay as previously described (Weislow et al., J. National Cancer Inst. 81: 577–586, (1989)). HIV-1 isolates included common laboratory stains (RF, III$_B$ and MN), as well as a panel of HIV-1 clinical isolates (Cushman et al., J. Med. Chem. 37: 3040–3050, (1994)). The pyridone-resistant HIV-1$_{A17}$ isolate (Nunberg et al., J. Virol., 65: 4887–4892 (1991)) was obtained from Emilio Emini at Merck Sharpe and Dohme Laboratories. Phytohemagglutinin-stimulated human peripheral blood lymphocytes (PBLs) and fresh monocyte-macrophage (Mono/MF) cultures were prepared and utilized in antiviral assays as previously described (Rice et al., Proc. Nat'l. Academy Science, USA 90: 9721–9724, (1993)); (Cushman et al., J. Med. Chem. 37: 3040–3050, (1994)). EC$_{50}$ values for these cultures indicate the drug concentration that provided a 50% reduction in viral p24 production. The experimental compounds (3'-azido-3'-deoxythymidine, AZT, NSC 602670; 1,2-dithiane or 1,2-dithiolanes listed in Table 1; KNI-272 protease inhibitor, NSC 651714; dextran sulfate, NSC 620255; UC38, NSC 638416) were derived from the NCI chemical repository. The compounds can be synthesized according to the teachings of Singh et al., Sulfur Letters 8: 107–114, (1988). The 4,5-cis-dihydroxy(1,1-dioxy-1,2,-dithiohexane) compound (NSC 624151) has been abbreviated as 624151 for convenience. MT-2, MT-4, U1, HeLa-CD4-LTR-β-gal and 174xCEM cells were obtained from the AIDS Research and Reference Program (National Institute of Allergy and Infectious Disease, National Institutes of Health, Bethesda, Md. USA), as were the HIV-2$_{MS}$ and the AZT-resistant HIV-1$_{G910-6}$ isolates.

U1 cells latently infected with two copies of HIV-1 proviral DNA per cell (Clous et al., J. Immunol. 142: 431–438, (1989)) were treated with 5 ng/ml tumor necrosis factor-α(TNF-α) for 24 hours to stimulate production of HIV-1 virions, after which various concentrations of 624151 were added to the cultures and incubated for an additional 48 hours. Cultures were analyzed for cell viability by the XTT reduction assay and cells were counted and scored for viability by trypan blue exclusion. Cells pellets were lysed (0.5% Triton X-100, 300 mM NaCl, 50 mM Tris-HCl, pH 7.6, 10 μg/ml each of Leupeptin and aprotinin (Boehringer Mannheim), 1.8 mg/ml iodoacetamide (Sigma Chemical Co., St. Louis, Mo.) and 1.0 mg/ml the protease inhibitor Pefabloc SC (Boehringer Mannheim at 4° C. for 15 min. and then quantitated for viral p24 content by ELISA. Cell-free supernatant samples were collected and analyzed for virus content by p24 ELISA, and infectivity in cultures of 174xCEM cells. Briefly, serial ½ dilutions of the supernatant were placed with 5×10$^3$ 174xCEM cells and cultured for 7 days, cell supernatants were analyzed for viral p24 content, and the number of infectious units/ml calculated. In addition, cell free supernatants were centrifuged at 17,000×g for 1 hour at 4° C. to collect virion pellets. Proteins from both the virion and cellular lysates were separated by 4–20% SDS-PAGE (50 μg protein per lane), blotted onto PVDF membranes, reacted with anti-p7 and anti-p24 antisera, and then probed with HRP-conjugated goat anti-rabbit IgG and subsequently viewed with Western Blot Chemiluminescence Reagent (Dupont NEN, Wilmington, Del.).

II. Combination Antiviral Analysis.

Analysis of drug combinations was performed utilizing the XTT assay described above, with statistical evaluations performed according to the method of Prichard and Shipman (Antiviral Res. 14: 181–206, (1990)). Combination antiviral XTT assays were performed with CEM-SS cells utilizing HIV-1$_{IIIB}$ as previously described (Buckheit et al., Antimicrobial Agents and Chemotherapy 39: 2718–2727, (1995)). The standard anti-HIV assay was altered for combination analysis by increasing the multiplicity of infection 3-fold, allowing greater statistical consistency in these assays.

III. Virus Attachment Assays.

Binding of HIV-1$_{RF}$ to PBLs was measured by a p24-based assay (Rice, et al., Proc. Nat'l. Academy of Science USA 90: 9721–9724, (1993)). Briefly, 5×10$^5$ PBLs were incubated with a concentrated stock of virus for 30 min. at 37° C. in the absence or presence of various concentrations of 624151, the unbound virus was washed away, and the cell-associated virus was solubilized in 1% Triton X-100, 1% BSA and analyzed by the p24 antigen capture assay as previously described. The binding of gp120 to CD4 was analyzed using an antigen capture ELISA. All steps of the assay were carried out according to the manufacturer's protocols.

IV. Enzymatic Assays.

The effects of 624151 on the in vitro activity of purified RT was determined by measurement of incorporation of [$^3$H]TTP onto the poly(rA):oligo(dT)(rAdT) or poly(rC):oligo(dG)(rCdG) homopolymer template/primer systems. Samples (5 μL) were blotted onto DE81 paper, washed with 5% dibasic sodium phosphate as previously described (Buckheit et al., Antiviral Res. 21:247, (1993)), and then quantitated on a Packard Matrix 9600 dual beam counter. 3'-Azido-3'-deoxythymidine-5'-triphosphate and UC38 (NSC 629243) served as positive controls for inhibition of RT. HIV-1 protease activity was quantitated by a reversed phase HPLC assay utilizing the Ala-Ser-Glu-Asn-Tyr-Pro-Ile-Val-Glu-Amide substrate (Multiple Peptide Systems, San Diego, Calif.) as previously described in Rice et al. (Proc. Nat'l. Academy of Science USA 9: 9721–9724, (1993)).

V. Zinc Finger Assays.

Fluorescence measurements of the Trp$^{37}$ residue in the C-terminal zinc finger of the recombinant HIV-1 p7NC protein were performed as previously described (Rice et al., Science 270:1194, 1995). The p7NC protein was prepared at 20 μg/ml in 10 mM sodium phosphate buffer (pH 7.0), treated with 25 μM of each compound, then after indicated time intervals the samples were diluted ¹⁄₁₀ in 10 mM sodium phosphate buffer (pH 7.0) and the fluorescence intensity measured. The excitation and emission wavelengths utilized with the Shimadzu RF5000 spectrofluorimeter were 280 nm and 351 nm, respectively. In an alternate assay, the zinc-selective fluorescent probe N-(6-methoxy-8quinolyl-)-p-toluenesulfonamide (TSQ, Molecular Probes, Eugene, Oreg.) originally described by Fredrickson (J. Neurosci. Meth. 20:91, 1987) was utilized to measure zinc released from the p7NC protein in vitro. Briefly, 2 μM recombinant HIV-1 p7NC protein in 10 mM sodium phosphate buffer, pH 7.0, 10% glycerol was treated with 10 μM 624151 (200 ml total volume in 96-well plates), and the time-dependent increase in fluorescence was measured on a Labsystems Fluoroskan II (360 nm excitation filter and 460 nm emission filter) over a period of 2 hours. Induction of alterations of p7NC proteins within intact virions involved treatment of HIV-1$_{MN}$ for 1 hour at 37° C. with 25 μM test compound. Samples were centrifuged 1 hour at 4° C. under 18,000×g to pellet the virus from the drug. Virus pellets were resolved by non-reducing SDS-PAGE and analyzed by immunoblot using monospecific rabbit antisera to the purified p7NC protein.

VI. Viral Inactivity Assay.

HeLa-CD4-LTR-βgal cells (1.5×10$^4$/well) were plated in 200 μl volume in flat bottom 96-well microtiter plates for 24 hours, after which the fluid was removed and replaced with drug-treated samples. The HIV-1$_{RF}$ stock was treated with various concentrations NSC 624151 for 2 hours at 37° C., followed by centrifugation (18,000×g for 1 hour at 4° C.) to remove compound from the virus, preparation of serial two-fold dilutions and plating of 200 μl of each dilution in triplicate onto the cell monolayer. The cultures were then incubated for 4 additional days, and monolayers were then fixed for 5 minutes with 2% formaldehyde/2% glutaraldehyde, washed twice with cold PBS and then stained with X-gal substrate for 24 hours at 37° C. The number of blue-stained cells (each indicating a single infectious unit) were then counted in each well and the number of infectious units per ml (mean±SD) of sample were determined values calculated.

VII. Saturated 1,2-dithiaheterocyclic compounds that inhibit HIV-1 replication.

Table 1 presents several exemplified saturated 1,2-dithiaheterocyclic compounds, specifically 1,2-dithiane or 1,2-dithiolane compounds, which can be used in compositions and methods of the present invention.

TABLE 1

Structure and Anti-HIV Activities of Saturated 1,2-Dithiaheterocyclic Compounds

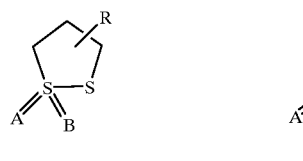

III      IV

| Class | NSC# | A | B | R | XTT Assay[a] EC$_{50}$ (μM) | IC$_{50}$ (μM) | Mo/MΦ EC$_{50}$ (μM) | IC$_{50}$ (μM) | Trp37 p7NC (%)[b] |
|---|---|---|---|---|---|---|---|---|---|
| III | 72270 | — | — | 4,4,-diCH$_2$OH | — | >200 | >100 | >100 | 5 |
| III | 661753 | O | — | 4,4,-diCH$_2$OH | — | >200 | 46 | >100 | 0 |
| III | 661127 | O | O | 4,4,-diCH$_2$OH | 34.0 | 378 | NA[c] | | |
| III | 660167 | — | — | 4,4,-diCH$_2$OAc | — | >200 | >100 | >100 | 0 |
| III | 661754 | O | — | 4,4,-diCH$_2$OAc | — | 14.3 | >100 | >100 | 12 |
| III | 661126 | O | O | 4,4,-diCH$_2$OAc | 9.8 | 30.3 | 21 | >100 | 82 |
| IV | 56224 | O | — | (No substituents) | — | 26.2 | >100 | >100 | 12 |
| IV | 627175 | O | O | (No substituents) | — | 5.7 | 25 | >100 | 45 |
| IV | 667089 | — | — | 4,5-di-OH (cis) | — | 20.1 | >100 | >100 | 4 |
| IV | 667090 | O | — | 4,5-di-OH (cis) | — | 103.3 | >100 | >100 | 0 |
| IV | 624151 | O | O | 4,5-di-OH (cis) | 6.6 | 184 | 8.0 | >100 | 78 |
| IV | 693194 | O | O | 4,5-di-OH (cis) (+ enantiomer) | 16 | 134 | | | |
| IV | 693195 | O | O | 4,5-di-OH (cis) (− enantiomer) | 8.8 | 132 | | | |
| IV | 667093 | — | — | 4,5-di-OAc (cis) | — | >200 | >100 | >100 | 0 |
| IV | 270423 | O | — | 4,5-di-OAc | — | — | | | |
| IV | 667091 | O | O | 4,5-di-OAc (cis) | — | 9.2 | 25 | >100 | 71 |
| IV | 663605 | — | — | 4,5-di-OH (trans) | — | >200 | >100 | >100 | 4 |
| IV | 663603 | O | — | 4,5-di-OH (trans) | — | 59.3 | >100 | >100 | 6 |
| IV | 624152 | O | O | 4,5-di-OH (trans) | 13.1 | 135 | 9.1 | >100 | 78 |
| IV | 667092 | — | — | 4,5-di-OAc (trans) | — | >200 | >100 | >100 | 0 |
| IV | 667094 | O | — | 4,5-di-OAc (trans) | — | 22.1 | 5.5 | >100 | 0 |
| IV | 624157 | O | O | 4,5-di-OSO$_2$PhMe (p) | — | — | — | — | — |
| III | 208744 | — | — | 4-(=NNHCONH2) | 28.7 | 127 | | | |
| III | 208750 | — | — | 4-spiro-hydantoin | 1.83 | 24.8 | | | |
| III | 212561 | — | — | 4-NH$_2$; 4-CO$_2$H | 3.06 | 10.7 | | | |
| III | 628502 | — | — | 3-(CH$_2$)$_4$CO$_2$H | 590 | >1210 | | | |
| III | 167127 | O | O | 4-COPh; 5-Ph | — | — | | | |
| IV | 663604 | O | O | 4,5-di-OAc (trans) | — | — | | | |

[a]The judgment of antiviral efficacy is based on the relative in vitro therapeutic index (IC$_{50}$/EC$_{50}$).
[b]The percent decrease in RFU was calculated based on measurement of the initial fluorescence of the p7NC protein before and 10 minutes after treatment with the 25 μM of compound at ambient temperature.
[c]NA indicates that no material was available for testing.

The 4,5-cis-dihydroxy (1,1-dioxy-1,2-dithiohexane compound (NSC 624151)) demonstrated antiviral activity in the XTT-based cytoprotection assay ($EC_{50}$=6.6 $\mu$M; $IC_{50}$=184 $\mu$M). In comparison to the cis-diol of 624151, the trans-diol form (NSC 624152) showed equivalent reactivity with the zinc fingers and only a slight reduction in the antiviral efficacy. Thus, the pharmaceutical compositions of the present invention encompass compounds of formulas (I) and (II) as either the cis or trans isomer. Removal of one (NSC 667090) or both (NSC 667092) of the oxygen atoms from the $S_1$ of 624151 resulted in essentially a complete loss of reactivity with the zinc fingers and complete abolition of antiviral activity. Interestingly, each of the compounds that effectively reacted with the zinc fingers also inhibited HIV-$1_{ADA}$ replication in the monocyte/macrophage model of infection.

Range of action studies with 624151 (Table 2) demonstrated that the compound effectively inhibited replication by typical laboratory strains of HIV-1 (RF, IIIB, SK1 and MN), including strains selected for resistance to AZT (HIV-$1_{6R}$), nevirapine (HIV-$1_{N119}$)pyridinone (HIV$1_{A17}$) and various other nonnucleoside RT inhibitors (NNRTIs). 624151 was also active against HIV-$1_{NL4-3}$ having selected site-directed mutations in the RT enzyme, and against clinical lymphotropic HIV-1 strains in lymphocyte cultures, monocytotropic HIV-1 strains in monocyte/macrophage cultures and all six clades (A–F) of HIV-1 tested, as well as against HIV-2 and SIV. Infection by HIV-$1_{IIIB}$ was also inhibited by 624151 in all cellular phenotypes tested.

TABLE 2

Range of Antiviral Action of NSC 624151

| | A | | | B | |
|---|---|---|---|---|---|
| Cell Type | Virus Strain | $EC_{50}$ ($\mu$M)[a] | Cell Type | Virus Strain | $EC_{50}$ ($\mu$M)[a] |
| | Laboratory HIV-1 | | | Clinical HIV-1 Isolates | |
| CEM-SS | RF | 6.6,13.0 | PBL | WEJO(SI)[c] | 7.59 |
| CEM-SS | IIIB | 20.8 | | ROJO(SI) | 25 |
| CEM-SS | SK1 | 22.7 | | BAKI(SI) | 19 |
| | Drug Resistant HIV-1 | | | VIHU(NSI) | 12 |
| MT-4 | 6R(AZT$^R$)[b] | 7.2 | | Monocytotropic HIV-1 | |
| MT-4 | A17(Pyr$^R$) | 13.0 | Mo/MΦ | Ba-L | 6.2 |
| CEM-SS | N119(Nev$^R$) | 18 | | ADA | 2.1 |
| MT-2 | Thiazol-108 | 17.0 | | HIV-I Clades | |
| | OC-100 | 12.7 | CEM-SS | Clade A | 22 |
| | TIBO-98/100 | 16.0 | | Clade B | 5.5 |
| | Calo-139 | 15.0 | | Clade C | 2.9 |
| | Calo-188 | — | | Clade D | 20 |
| | DPS-181 | 16.5 | | Clade E | — |
| | UC38-181 | 17.0 | | Clade F | 69 |
| | E-BPTU-181 | 17.0 | | Other Retroviruses | |
| | HEPT-236 | 16.0 | CEM-SS | HIV-$2_{ROD}$ | 15.6 |
| | NL4-3 Site-Directed RT Mutants | | | SIV | 22 |
| MT-2 | None | 16.6 | | Cell (type) Virus[d] | |
| | L74V | 19.8 | CEM-SS (T) | HIV-1IIIB | 6.1 |
| | A986 | 26.5 | H9(T) | | 13 |
| | K103N | 17.3 | U937(M) | | 3.2 |
| | V1061 | 20.8 | MT-2(T) | | 18.8 |
| | V1081 | 20.0 | AA5(B, EBV+) | | 26 |
| | V179D | 20.2 | | | |
| | Y181C | 20.9 | | | |
| | Y188C | 19.4 | | | |
| | 4XAZT | 10.7 | | | |

[a]Anti-HIV studies utilizing lymphocyte-derived cell lines were performed using the XTT cytopathicity assay, while antiviral assays utilizing PBL or Mono/MΦ cultures were performed by measurement of cell-free p24 levels.
[b]AZT$^R$, Pyr$^R$ and Nev$^R$ indicate strains of HIV-1 that are resistant to AZT, pyridinone or nevirapine, respectively.
[c]SI and NSI refer to synctyia inducing and non-synctyia inducing strains of HIV-1, respectively.
[d]T, B and EBV refer to T and B cell lineage and Epstein-Barr virus, respectively. The XTT cytoprotection studies with HIV-1 were confirmed by measurement of supernatant RT, p24 and infectious virus titers.

To determine if the inhibitory action of 624151 was adversely affected by the multiplicity of infection (MOI) of the input virus, we measured the $EC_{50}$ of the compound in cultures of CEM-SS cells infected with HIV-$1_{IIIB}$ at MOIs ranging from 0.01 to 0.32 (Table 3). At the typical MOI of 0.01, the 624151 had an $EC_{50}$=8.4 $\mu$M, and at the highest MOI of 0.32, the $EC_{50}$ had only increased to 21.0 $\mu$M. These data indicated that 624151 is relatively resistant to the effects of increasing the viral MOI. This is in contrast to results with AZT, for which the $EC_{50}$ was 18.9 nM at the lowest MOI but was completely inactive after only a six-fold increase in the MOI.

TABLE 3

NSC 624151 is Resistant to the Effects of Increasing the Viral Multiplicity of Infection

| | Amount HIV-$1_{RF}$ | | $EC_{50}$ |
|---|---|---|---|
| MOI | ($\mu$l)/well | AZT ($\mu$M) | NSC 624151 ($\mu$M) |
| 0.32 | 50 | >10 | 21 |
| 0.16 | 25 | >10 | 21.3 |
| 0.08 | 12.5 | >10 | 27.7 |
| 0.04 | 6.25 | 1.57 | 16.8 |
| 0.02 | 6.125 | 0.024 | 17.1 |
| 0.01 | 1.5625 | 0.019 | 8.4 |

Finally, 624151 was tested in combination with AZT, ddC, 3TC, Costatolide or the KNI-272 protease inhibitor, and the data were evaluated by the method of Prichard and Shipman, Antiviral Res. 14:181–206, (1990). The synergy volumes for the combinatorial anti-HIV activities calculated at the 95% confidence level were 37, 80, 44, 55 and 16 $\mu$M$^2$, respectively, for each combination. Synergy volumes that range from 0 to 50% represent additivity and volumes>50% represent synergistic responses. Therefore, 624151 acted in an additive to slightly synergistic response in combination with other antiviral agents, but was not antagonistic with any agents tested. Thus, it is anticipated that the present dithiane dioxide compounds can be used in pharmaceutical compositions further including other antiviral agents.

VIII. NSC 624151 Reacts With the p7NC Protein Zinc Fingers.

Figure 1B:
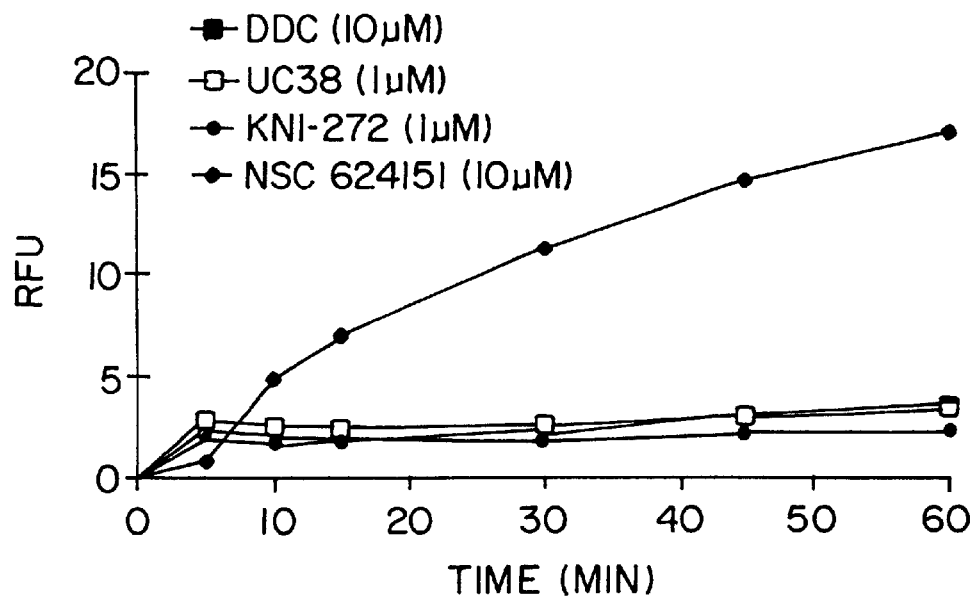
FIG. 1(B) is a graph which illustrates binding of ejected zinc by TSQ fluorochrome.

The ability of 624151 to chemically interact with the zinc fingers of the HIV-1 p7NC protein was initially determined by a fluorescence assay (Rice et al., Science 270:1194–1197, (1995)) that measures a loss in intrinsic fluorescence of the tryptophan (Trp$^{37}$) residue in the second finger of the protein that occurs upon loss of zinc from the finger (Summers et al., Protein Sci. 1:563, 1992). FIG. 1(A) illustrates the time-dependent loss of fluorescence caused by the 624151 but not by the AZT control. The ability of 624151 to promote zinc ejection from the p7NC protein in vitro was confirmed with an assay that utilizes a zinc chelator that fluoresces upon binding of zinc. As the 624151 modifies the zinc finger thiolates and the zinc is ejected over time, the metal is bound by the TSQ fluorochrome (FIG. 1(B)).

Although 624151 reacted aggressively with the p7NC protein zinc fingers, the compound was without an effect on other facets of the viral replication cycle. Data in Table 4 establish that 624151 did not inhibit the attachment of HIV-1 virions to target cells, the fusion or target cells expressing CD4 and gp120, or the direct interaction between purified gp120 and CD4 molecules, each of which is considered a surface event. Likewise, the enzymatic activities of the purified HIV-1 p66-p51 RT enzyme (utilizing both the rAdT and rCdG template/primer systems) and the purified HIV-1 protease and integrase enzymes were not inhibited by 624151. Thus, the antiviral mechanism of action of 624151 correlated only with interaction with the retroviral zinc finger.

TABLE 4

Mechanism of Action Studies of NSC 624151 Dithiane

| Infection* | | EC$_{50}$ ($\mu$M) | 7.85 ± 5.5 (Mean ± S.D., n = 6) |
|---|---|---|---|
| Attachment$^\dagger$ | | ID$_{50}$ ($\mu$M) | NI$^\ddagger$ |
| Fusion | | ID$_{50}$ ($\mu$M) | NI |
| gp120-CD4 | | ID$_{50}$ ($\mu$M) | NI |
| RT Activity | rAdT | ID$_{50}$ ($\mu$M) | NI |
| | rCdG | ID$_{50}$ ($\mu$M) | NI |
| Protease Activity | | ID$_{50}$ ($\mu$M) | NI |
| Integrase | | ID$_{50}$ ($\mu$M) | NI |

*Antiviral assays were performed using the XTT cytopathicity assay.
$^\dagger$Attachment of HIV-1 to fresh human PBLs, binding of gp120 to CD4, and the effects of compounds on HIV-1 RT and protease were quantitated as described in Materials and Methods. ID$_{50}$ values (drug concentration providing 50% inhibition of the indicated activity) were derived from graphs in which each point represented the mean of at least three replicates. As controls, AZT-triphosphate inhibited RT activity with an ID$_{50}$ = 27 nM (non-phosphorylated AZT was not inhibitory), the KNI-272 protease inhibitor reduced protease activity with an ID$_{50}$ = 3 nM, and dextran sulfate inhibited virion binding with an ID$_{50}$ = 1.8 $\mu$g/ml.
$^\ddagger$NI indicates that no inhibition was observed at the high test concentration (100 $\mu$M) of compounds.

IX. Action of 624151 on Intact HIV-1 Virions.

Figure 2A:
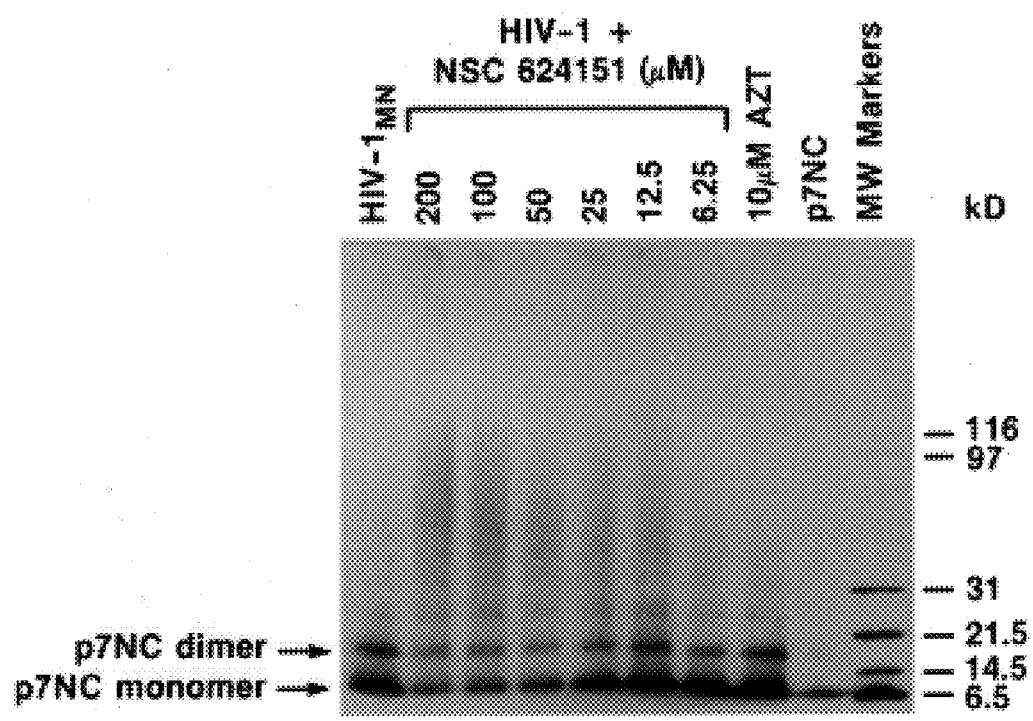
FIG. 2(A) is a photograph of an immunoblot which demonstrates the ability of NSC 624151 to enter intact virions and cause disulfide cross-linkage between virion NC proteins.
Figure 2B:
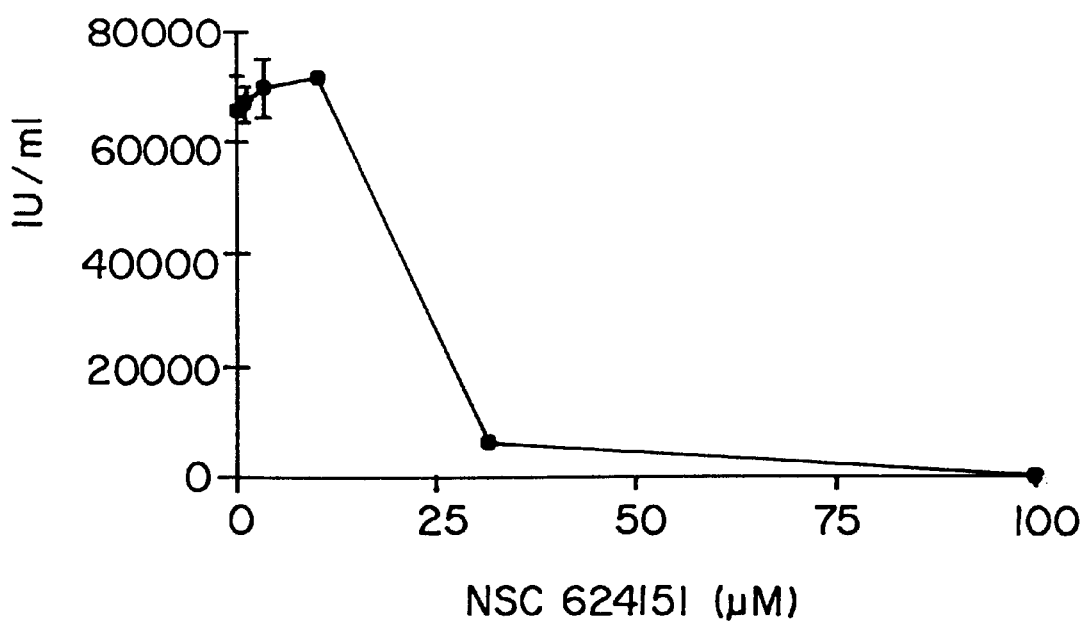
FIG. 2(B) is a graph which demonstrates the ability of NSC 624151 to enter intact virions and inactivate the viral infectivity.

In order to determine if the 624151 entered intact HIV-1 virions and affected the p7NC protein zinc fingers, purified HIV-1$_{MN}$ was treated with increasing concentrations of the compound and the viral proteins were then separated by non-reducing SDS-PAGE and immunoblotted with mono-specific antisera to the p7NC protein (FIG. 2(A)). This type of analysis revealed decreases in the amounts of detectable virion p7NC following treatment with the 624151, and no interactions with other proteins was observed. The p7NC protein was not lost but rather resolved as higher molecular weight aggregates due to the formation of disulfide bridges between the zinc fingers of closely approximated p7NC molecules within the virus; no alterations in the virion p7NC profile were observed when the samples were electrophoresed under reducing conditions (not shown). Moreover, treatment of HIV-1$_{RF}$ virions with 624151 resulted in a concentration-dependant inactivation of viral infectivity (FIG. 2(B)). Thus, 624151 effectively entered and inactivated cell-free HIV-1 virions by chemically attacking the p7NC CCHC zinc fingers and promoting cross-linkage among the p7NC proteins.

X. Influence of 624151 on Virus Production From Cells Latently Infected with HIV-1.

Figure 3A:
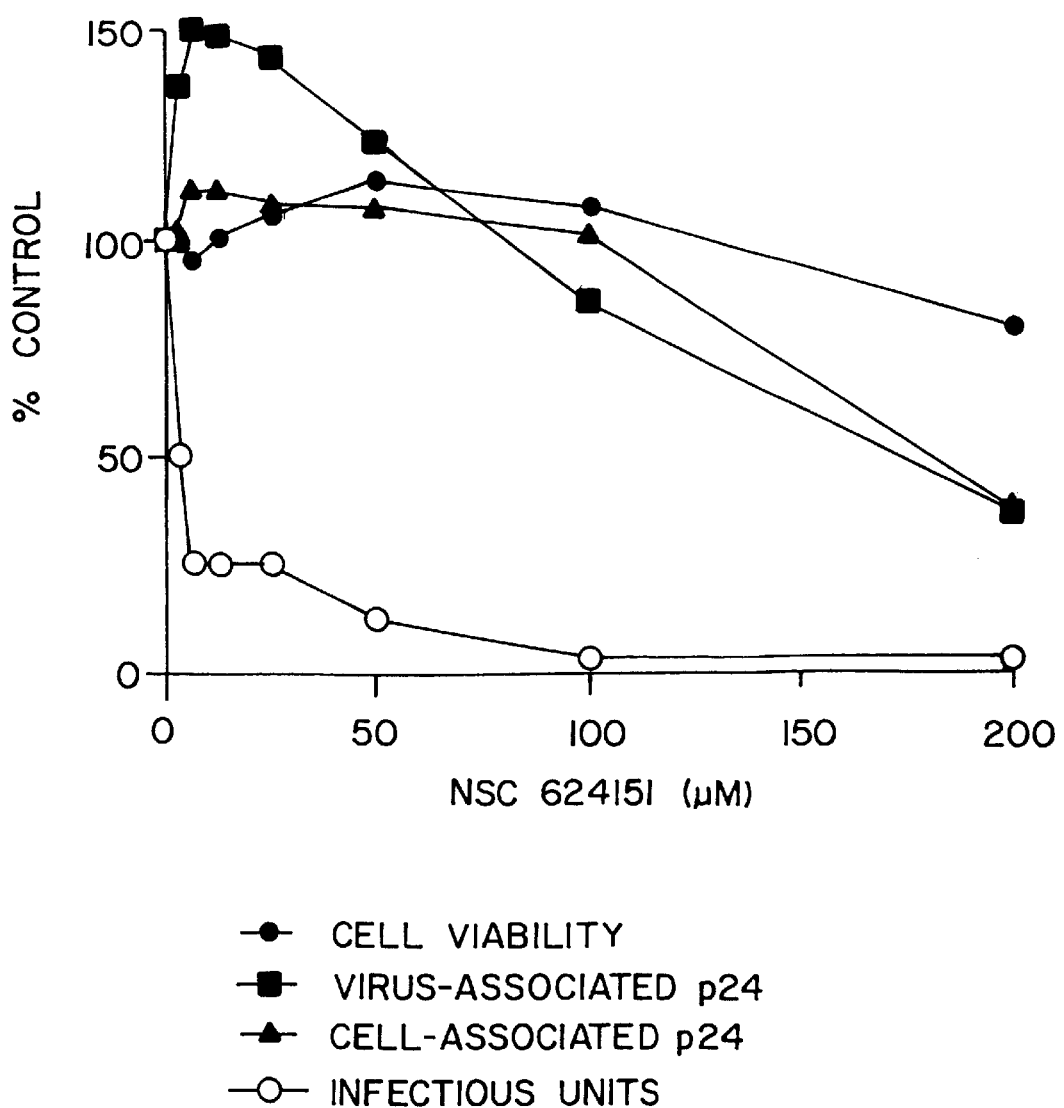
FIG. 3(A) is a graph which illustrates that one action of NSC 624151 is through the inhibition of the formation of infectious virus from HIV-1 infected cells.

Once proviral DNA has integrated into the cellular DNA, compounds that act on replicative events during the pre-integrative phase of infection are without effect. However, the zinc fingers as a part of the Pr55$^{gag}$ and Pr160$^{gag-pol}$ participate in the post-integrative phase production of progeny infectious virions, and the zinc finger-reactive 624151 should affect those functions. To test this possibility, we evaluated the effects of 624151 on cell viability and the production of viral proteins and infectious virions from U1 cells that latently harbor two copies of HIV-1 proviral DNA. Stimulation of U1 cells with TNF-α results in the production of high levels of p24 and infectious virions. Addition of 624151 to the stimulated U1 cultures (FIG. 3(A)) did not significantly reduce cell viability (XTT) or cell number and did not dramatically reduce the levels of intracellular or extracellular viral p24. However, the infectious titer of virions released from the U1 cells was effectively reduced when concentrations of 624151 as low a 3 $\mu$M were administered. Thus, 624151 results in prevention of the formation of infectious virus from previously infected cells.

Figure 3B:
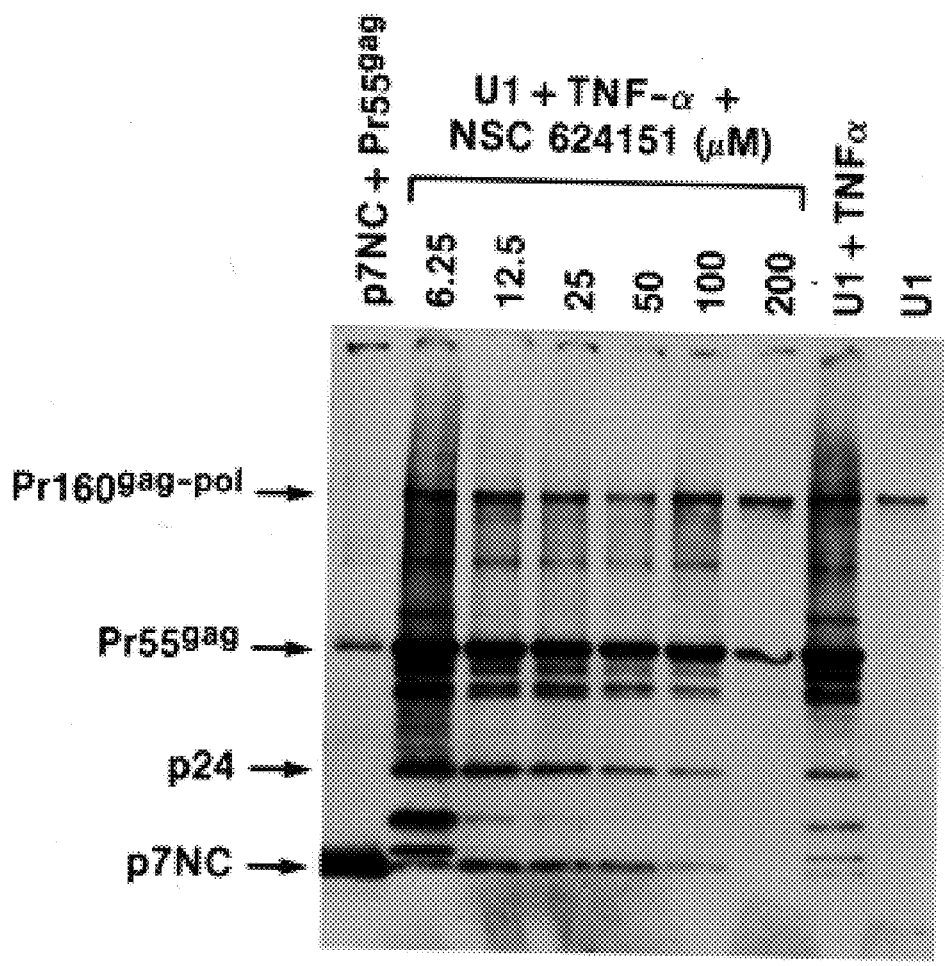
FIG. 3(B) is a photograph of an immunoblot which presents non-reducing SDS-PAGE analysis of the mechanism of action of NSC 624151. Cross-linkage of viral zinc finger proteins inside the infected cells prevents processing of precursor proteins to mature viral proteins.

To gain a better understanding of the effects of 624151 on the late phase event of virion production, we investigated the nature of viral proteins in the U1 system by immunoblot analysis. As described above, U1 cells were induced with TNF-α for 24 hours, various concentrations of 624151 added for an additional 48 hours, and then cells collected. Cell pellets were lysed, resolved by non-reducing SDS-PAGE and immunoblotted for p7 and p24 proteins (FIG. 3(B)). Increasing concentrations of 624151 resulted in a decrease in Pr55$^{gag}$ processing to the p41, p24, p9 and p7 proteins, even though the precursor was synthesized in normal amounts. Equivalent results were observed with the viral lysates, and the 624151 was found not to inhibit purified HIV-1 protease, as assessed by the ability of the protease to process purified recombinant Pr55$^{gag}$ (data not shown). Together, these data indicated that within infected U1 cells the 624151 compound acts on the zinc finger of the processed p7NC protein and the Gag precursor polypeptides, resulting in defective Gag precursor processing and rendering the release virus inactive.

XI. Stereospecificity of Antiviral Activity of cis-1,1-dioxo[1,2]dithiane-4,5-diol
The XTT Assay Racemate and enantiomers of the cis-1,1-dioxo[1,2] dithiane-4,5-diol were synthesized and evaluated for antiviral activity in the XTT assay as described hereinabove. The results for these and control compounds are shown in Table 5 below.

TABLE 5

| | XTT Assay | | | |
|---|---|---|---|---|
| | EC$_{50}$ | | IC$_{50}$ | |
| NSC No. | Duplicates | Mean | Duplicates | Mean |
| AZT (nM) | 5.4, 5.7 | 5.6 nM | >1000, >100 | >1000 nM |
| dextran sulfate ($\mu$g/ml) | 0.45, 1.07 | 0.76 $\mu$g/ml | >95, >95 | >95 $\mu$g/ml |
| 624151 ($\mu$M) racemate | 9.53, 14.9 | 12.2 $\mu$M | 116, 127 | 122 $\mu$M |

TABLE 5-continued

XTT Assay

| | EC$_{50}$ | | IC$_{50}$ | |
|---|---|---|---|---|
| NSC No. | Duplicates | Mean | Duplicates | Mean |
| 693194 (μM) (+) enantiomer | 18.6, 13.7 | 16.2 μM | 134, 133 | 134 μM |
| 693195 (μM) (−) enantiomer | 9.04, 8.64 | 8.8 μM | 129, 135 | 132 μM |

The EC$_{50}$ values for the racemate and enantiomers of the cis-1,1-dioxo[1,2]dithiane-4,5-diol are of similar magnitude, and all are active. Interestingly, the (−) enantiomer (NSC 693195) had an EC$_{50}$ about half that of the (+) enantiomer (NSC 693194). Also, the average of these EC$_{50}$s is equivalent to the EC$_{50}$ for the racemic mixture (NSC 624151). There were no apparent differences in the toxicities.

Mechanistic Evaluations Against Various Molecular Targets

The racemate and each enantiomer were tested for inhibition of the in vitro activities of virus attachment to cells, HIV-1 reverse transcriptase (RT), HIV-1 protease (Pr), HIV-1 integrase (In), and HIV-1 nucleocapsid p7 (p7NC) protein. As shown in Table 6, none of the compounds inhibited attachment, RT, Pr or In. In contrast, each modified the p7NC zinc finger motifs at essentially equivalent rates in the Trp37 zinc ejection assay.

TABLE 6

Molecular Target-Based Assays

| | | | | | p7NC Trp37 Assay (RFU)[a] | | | |
|---|---|---|---|---|---|---|---|---|
| NSC # | Attachment | RT | Pr | In | 0 | 3 | 10 | 30 min. |
| 624151 racemate | [b]NI$_{100 \mu M}$ | NI$_{100 \mu M}$ | NI$_{100 \mu M}$ | NI$_{100 \mu M}$ | 295 | 136 | 75 | 42 |
| 693194 (+) enantiomer | NI$_{100 \mu M}$ | NI$_{100 \mu M}$ | NI$_{100 \mu M}$ | NI$_{100 \mu M}$ | 280 | 146 | 75 | 41 |
| 693195 (−) enantiomer | NI$_{100 \mu M}$ | NI$_{100 \mu M}$ | NI$_{100 \mu M}$ | NI$_{100 \mu M}$ | 279 | 117 | 69 | 45 |

[a]The purified recombinant p7NC protein at 20 μg/ml in 10 mM Sodium Phosphate buffer, pH 7.0 in 1 ml was treated with 25 μM of compound. At indicated times, the mixture was diluted 1/10 and the relative fluorescence units (RFU) measured in a Shimadzu RF5000 spectrofluorimeter with $\lambda_{Em}$ = 280 mn and $\lambda_{Em}$ = 351 mn. Following loss of zinc from the C-terminal zinc finger, the Trp37 residue folds away from the aqueous environment and experiences a loss of fluorescence.
[b]NI$_{100 \mu M}$ indicates that no inhibition of the indicated activity was observed at the high test concentration of 100 μM.

XII. Resolution of cis-4,5-dihydroxy-1,2-dithiane 1,1-dioxide
Mosher diesters of cis 1,2-dithiane 1,1 dioxide.

To (+/−)-cis-4,5-dihydroxy-1,2-dithiane 1,1-dioxide (0.225 g, 1.22 mmol) and N,N-dimethylaminopyridine (0.597 g, 4.89 mmol) in dry CH$_2$Cl$_2$ (5 mL) was added (R)-(−)-α-methoxy-α-(trifluoromethyl)phenylacetyl chloride (0.750 g, 2.97 mmol) over 30 minutes at 0° C. under N$_2$. The reaction mixture was allowed to gradually rise to room temperature and stirred at that temperature for 20 h. Then, the reaction mixture was cooled in an ice bath, washed with 1 N HCl, followed by saturated NaHCO$_3$ and finally with distilled H$_2$O. The CH$_2$Cl$_2$ layer was dried with anhydrous Na$_2$SO$_4$, concentrated and separated on a silica gel column with hexanesethyl acetate (85:15) to obtain the first diastereomer of the Mosher diester of cis 1,2-dithiane 1,1 dioxide (0.252 g, 34%) as the first fraction; mp: 162–163° C.; [α]$^{21}$D=+81°(CH$_2$Cl$_2$, c1.0); $^1$H NMR(CDCl$_3$) δ7.39(m, 10H), 5.79 (m, 1H). 5.59 (m, 1H), 3.67 (m, 3H), 3.49 (s, 3H), 3.40 (dd, 1H, J=15.5 Hz, J=5.1 Hz), 3.25 (s, 3H); $^{13}$C NMR(CDCl$_3$) δ165.35, 165.19, 131.29, 131.14, 130.10, 129.95, 128.77, 128.61, 126.91, 125.16, 120.59, 116.02, 85.40, 84.94, 84.44, 84.01, 70.78, 65.73, 58.47, 55.52, 55.38, 34.15. Elemental analysis: Calculated for C$_{24}$H$_{22}$F$_6$O$_8$S$_2$: C 46.75, H 3.60, S 10.40. Found C 46.79, H3.58, S 10.29. The second fraction yielded the second diastereomer of the Mosher diester of cis 1,2-dithiane 1,1 dioxide (0.250 g, 33%) as white crystals: mp: 184–185° C.; [α]$^{21}$D=120°(CH$_2$Cl$_2$, c 1.0); $^1$H NMR (CDCl$_3$) δ7.38 (m, 10H), 5.76 (m, 2H), 3.73 (d, 1H, J=15.4Hz), 3.54 (m, 3H), 3.45 (s, 3H), 3.40 (s, 3H); $^{13}$C NMR (CDCl$_3$) δ165.41, 165.31, 131.17, 131.07, 130.07, 130.01, 128.73, 128.65, 127.31, 126.96, 125.27, 125.18, 120.67, 120.58, 116.09, 115.97, 85.38, 84.93, 84.48, 84.03, 70.84, 66.28, 58.36, 55.58, 55.32, 34.47. Elemental analysis: Calculated for C$_{24}$H$_{22}$F$_6$O$_8$S$_2$: C 46.75, H 3.60, S 10.40. Found C 46.68, H 3.66, S 10.32.

(+)-cis-4,5-Dihydroxy-1,2-dithiane 1,1-dioxide

To the first diastereomer of the Mosher diester of cis 1,2-dithiane 1,1 dioxide (0.167 g. 0.271 mmol) was added 40% NH$_3$ in MeOH (4 mL) over 5 minutes under N$_2$ at room temperature. The solid went into solution as 40% NH$_3$ in MeOH was added and the reaction mixture turned pale yellow in color. After the reaction mixture was stirred for 1.5 h, TLC showed complete disappearance of the diester. The reaction mixture was then concentrated under vacuum and the crude oil was separated on a silica gel column using CH$_2$Cl$_2$-MeOH (95:5) as the eluent to obtain (+)-cis-4,5-dihydroxy-1,2-dithiane 1,1-dioxide (0.0212 g, 43%) as a white solid: mp 133–134° C.; [α]$^{21}$$_D$=+151°; $^1$H NMR (CD$_3$OD) δ4.20 (m, 1H), 4.13 (m, 1H), 3.66 (dd, 1H, J=12.6 Hz, J=11.0 Hz), 3.47 (dd, 1H, J=14.7 Hz, J=1.4 Hz), 3.37 (m, 2H); $^{13}$C NMR (CD$_3$OD) δ71.44, 65.92, 61.62, 38.63.

(−)-cis-4,5-Dihydroxy-1,2-dithiane 1,1-dioxide

To the second diastereomer of the Mosher diester of cis 1,2-dithiane 1,1 dioxide (0.159 g, 0.258 mmol) was added 40% NH$_3$ in MeOH (4 mL) over 5 minutes under N$_2$ at room temperature. The solid went into solution as 40% NH$_3$ in MeOH was added and the reaction mixture turned pale yellow in color. After the reaction mixture was stirred for 1.5 h, TLC showed complete disappearance of the diester. The reaction mixture was then concentrated under vacuum and the crude oil was separated on a silica gel column using CH$_2$Cl$_2$-MeOH (95:5) as the eluent to obtain (−)-cis-4,5-dihydroxy-1,2-dithiane 1,1-dioxide (0.019 g, 40%) as a white solid: mp 131–132° C.; [α]$^{21}$$_D$=−146°; $^1$H NMR (CD₃OD) δ4.19 (m, 1H), 4.13 (m, 1H), 3.66 (dd, 1H, J=12.8 Hz, J=10.9 Hz), 3.47 (dd, 1H, J=14.7 Hz, J=1.5 Hz), 3.37 (m, 2H); ¹³C NMR (CD₃OD) δ71.42, 65.91, 61.62, 38.63.

The invention has been described with reference to various specific and preferred embodiments and techniques. However, it should be understood that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually indicated by reference.

We claim:

1. A method of inhibiting retrovirus replication comprising exposing said retrovirus to an effect amount of a pharmaceutical composition comprising (i) pharmaceutically acceptable carrier, and (ii) saturated 1,2-dithiaheterocyclic compound, pharmaceutically acceptable salt thereof, or a mixture thereof;

wherein the saturated 1,2-dithiaheterocyclic compound is a 1,2-dithiane or 1,2 dithiolane compound, and the saturated 1,2-dithiaheterocyclic compound comprises a ring sulfur atom present in a —S(O)— or —SO₂— oxidation state.

2. The method of claim 1 wherein the saturated 1,2-dithiaheterocyclic compound includes at least one ring carbon atom including a substituent selected from the group consisting of hydroxy, hydroxyalkyl, alkyl, cycloalkyl, acyl, alkoxy, cycloalkoxy, carboxyalkyl, acyloxyalkyl, —C(O)OH, —C(O)O—R⁵, acyloxy, aryl, —OSO₂R⁶, and —NR⁷R⁸, wherein R⁵ and R⁶ are independently alkyl, cycloalkyl or aryl, and R⁷ and R⁸ are independently hydrogen, alkyl, cycloalkyl or aryl.

3. A method of inactivating retrovirus in a body fluid comprising exposing said body fluid to an effective amount of a pharmaceutical composition to inactivate the retrovirus;

wherein the pharmaceutical composition comprises (i) pharmaceutically acceptable carrier, and (ii) saturated 1,2-dithiaheterocyclic compound, pharmaceutically acceptable salt thereof, or a mixture thereof; and the saturated 1,2-dithiaheterocyclic compound is a 1,2-dithiane or 1,2 dithiolane compound, and the saturated 1,2-dithiaheterocyclic compound comprises a ring sulfur atom present in a —S(O)— or —SO₂— oxidation state.

4. A method of treating viral disease in a patient comprising administering an effective amount of a pharmaceutical composition to the patient;

wherein the pharmaceutical composition comprises (i) pharmaceutically acceptable carrier, and (ii) saturated 1,2-dithiaheterocyclic compound, pharmaceutically acceptable salt thereof, or a mixture thereof; and the saturated 1,2-dithiaheterocyclic compound is a 1,2-dithiane or 1,2 dithiolane compound, and the saturated 1,2-dithiaheterocyclic compound a ring sulfur atom present in a —S(O)— or —SO₂— oxidation state.

5. The method of claim 4 wherein the viral disease is caused by infection by HIV-1, HIV-2, SIV, BIV, EIAV, Visna, CaEV, HTLV-1, BLV, MPMV, MMTV, RSV, MuLV, FeLV, BaEV, or SSV.

6. A kit for treating a viral infection comprising:
   (i) a vessel containing an effective antiviral amount of a pharmaceutical composition; and
   (ii) instructions for using the composition for treating a viral infection;

wherein the pharmaceutical composition comprises (i) pharmaceutically acceptable carrier, and (ii) saturated 1,2-dithiaheterocyclic compound, pharmaceutically acceptable salt thereof, or a mixture thereof; and the saturated 1,2-dithiaheterocyclic compound is a 1,2-dithiane or 1,2 dithiolane compound, and the saturated 1,2-dithiaheterocyclic compound comprises a ring sulfur atom present in a —S(O)— or —SO₂— oxidation state.

7. A pharmaceutical composition comprising (i) pharmaceutically acceptable carrier; and (ii) saturated 1,2-dithiolane compound, pharmaceutically acceptable salt thereof, or a mixture thereof, wherein the 1,2-dithiolane compound has the formula:

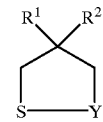

wherein R¹ and R² are independently hydroxyalkyl or acyloxyalkyl; and Y is —S(O)— or —SO₂—.

8. The pharmaceutical composition of claim 7 wherein R¹ and R² are independently C(1)–C(3)hydroxyalkyl or C(2)–C(4)acyloxyalkyl.

9. The pharmaceutical composition of claim 8 wherein R¹ and R² are independently —CH₂OH or —CH₂OAc.

10. The pharmaceutical composition of claim 7 wherein Y is —SO₂—.

11. The pharmaceutical composition of claim 7 wherein R¹ and R² are —CH₂OH.

12. A pharmaceutical composition comprising (i) pharmaceutically acceptable carrier; and (ii) saturated 1,2-dithiane compound, pharmaceutically acceptable salt thereof, or a mixture thereof, wherein the 1,2-dithiane compound has the formula:

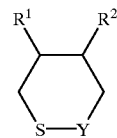

wherein R¹ and R² are independently hydrogen, hydroxy, hydroxyalkyl, acyloxy, acyloxyalkyl or OSO₂R⁶, and R⁶ is alkyl, cycloalkyl or aryl; and Y is —S(O)— or —SO₂—.

13. The pharmaceutical composition of claim 12 wherein R¹ and R² are independently C(1)–C(3)hydroxyalkyl, or C(2)–C(4)acyloxyalkyl.

14. The pharmaceutical composition of claim 12 wherein R¹ and R² are independently hydroxy or acetoxy.

15. The pharmaceutical composition of claim 12 wherein R¹ and R² are —CH₂OH, and Y is —SO₂—.

16. The pharmaceutical composition of claim 12 wherein the 1,2-dithiane compound has the formula:

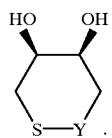

17. The pharmaceutical composition of claim 16 wherein Y is —SO$_2$—.

18. The pharmaceutical composition of claim 12, further comprising a nucleoside analog, a protease inhibitor, or a mixture thereof.

19. The pharmaceutical composition of claim 12, further comprising an antiviral agent, a spermicidal agent, a bactericidal agent, or a mixture thereof.

20. A pharmaceutical composition comprising (i) pharmaceutically acceptable carrier; and (ii) saturated 1,2-dithiolane compound, pharmaceutically acceptable salt thereof, or a mixture thereof, wherein the 1,2-dithiolane compound has the formula:

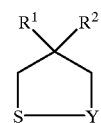

wherein Y is —S—, —S(O)— or —SO$_2$—; and
R$^1$ and R$^2$ together are =N—NH—C(O)—NH$_2$; or
R$^1$ and R$^2$ together are —NH—C(O)—NH—C(O)—; or
R$^1$ is —NH$_2$ and R$^2$ is —CO$_2$H.

21. A method of preparing a chiral cis-4,5-dihydroxy-1,2-dithiane, 1,1-dioxide comprising:
 (i) reacting a chiral cis4,5dihydroxy-1,2-dithiane 1,1-dioxide with (R)-(−)-α-methoxy-α-(trifluoromethyl) phenylacetyl chloride to form a Mosher diester of cis1,2-dithiane 1,1 dioxide;
 (ii) separating the diastereomers of the Mosher diester of cis1,2dithiane 1,1 dioxide; and
 (iii) hydrolzying a diasteromer of the ester to form a chiral cis-4,5-dihydroxy-1,2-dithiane 1,1-dioxide.

* * * * *